United States Patent [19]

Schwartz

[11] Patent Number: 4,607,897

[45] Date of Patent: Aug. 26, 1986

[54] VIDEOENDOSCOPIC SUPPORT STAND

[76] Inventor: C. Bruce Schwartz, 6594 Mill Creek Rd., The Dalles, Oreg. 97058

[21] Appl. No.: 752,629

[22] Filed: Jul. 8, 1985

[51] Int. Cl.[4] .............................................. A47B 81/00
[52] U.S. Cl. .................. 312/209; 248/188.7; 248/282; 312/250; 312/7.2
[58] Field of Search .............................. 433/108, 109; 248/188.7, 250, 282; 312/251, 250, 249, 209, 7.2

[56] References Cited

U.S. PATENT DOCUMENTS

| | | | |
|---|---|---|---|
| 2,164,390 | 7/1939 | Dikerson | 248/282 |
| 3,233,517 | 2/1966 | Morrison | 248/188.7 |
| 3,550,892 | 12/1970 | Propst | 248/282 |
| 3,636,633 | 1/1972 | Fuller et al. | 433/108 |
| 4,013,328 | 3/1977 | Wolf et al. | 312/209 |
| 4,546,708 | 10/1985 | Wilbruth | 248/282 |

*Primary Examiner*—James T. McCall
*Attorney, Agent, or Firm*—Klarquist, Sparkman, Campbell, Leigh & Whinston

[57] ABSTRACT

A videoendoscopic support stand includes a cabinet pivotally mounted on a vertical support column and rotatable between first and second positions. A television monitor is disposed on a tray supported on an arm pivotally mounted atop the support column. The television support arm is rotatable between first and second positions which are on the opposite side of the support column from the first and second cabinet positions such that the center of gravity of the entire stand and equipment always lies within the support area of the base.

9 Claims, 6 Drawing Figures

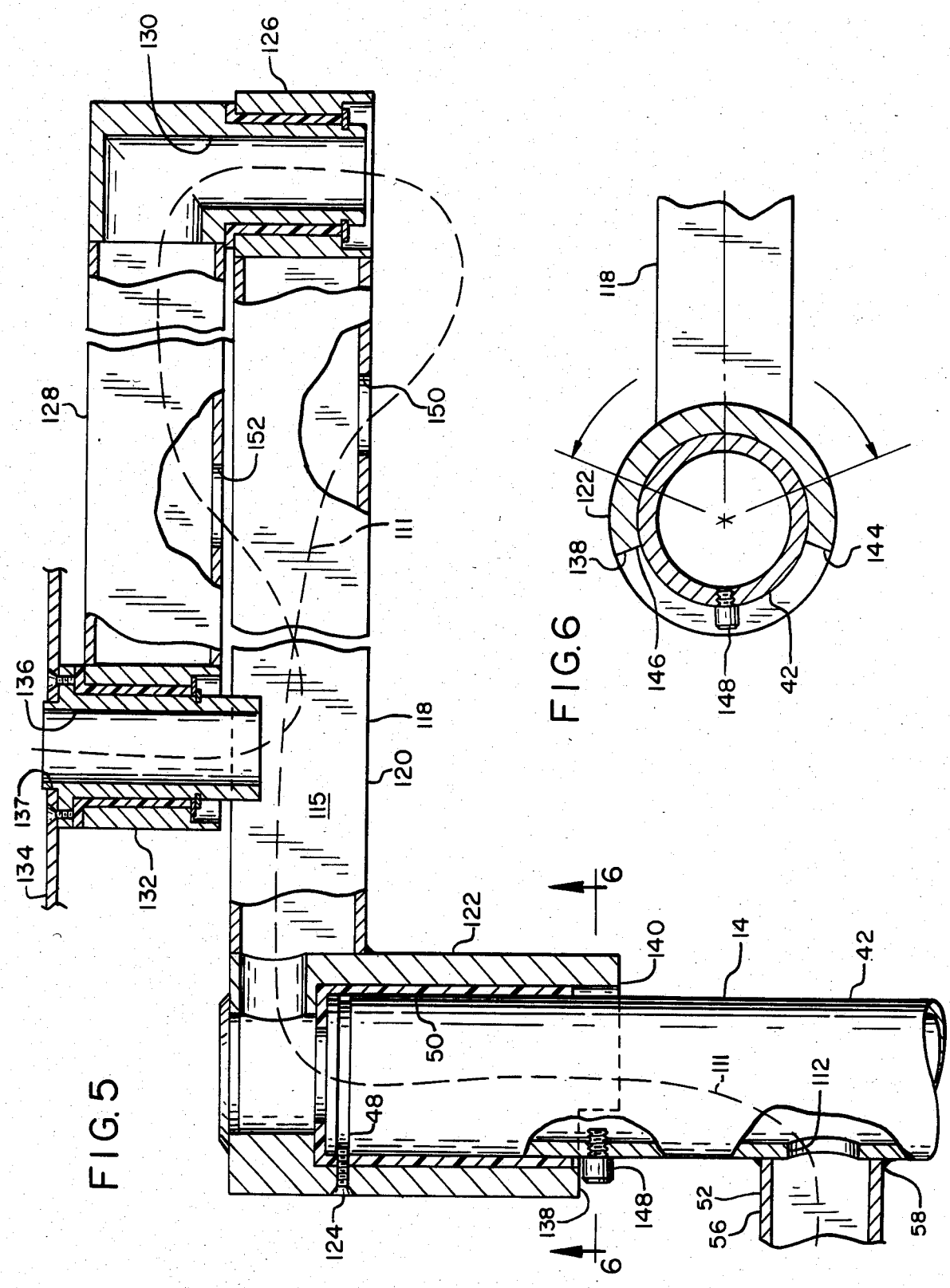

4,607,897

VIDEOENDOSCOPIC SUPPORT STAND

BACKGROUND OF THE INVENTION

This invention relates to surgical operating room furniture and equipment and more particularly, to apparatus for supporting equipment for use in performing videoendoscopic medical procedures.

Videoendoscopic medical procedures encompass a wide variety of procedures including arthroscopy, laporoscopy, bronchoscopy, nephroscopy, cystoscopy, gastroenteroscopy and operating microscopy. The equipment typically includes a television monitor, camera apparatus including a signal generator for the camera, a light source, video recorder, an insufflator, and cautery and other equipment used for specific videoendoscopic procedures. Cabinetry suitable for housing the equipment must be easily mobile so that it can be used on either side of an operating table. The television monitor must be movable so that it may be placed in optimal positions for viewing by the user.

A known support stand particularly desirable for supporting arthroscopy equipment including a television camera, a television monitor and saline fluid bags is disclosed in my related application U.S. Ser. No. 578,221, filed Feb. 8, 1984, ARTHROSCOPY SUPPORT STAND, now U.S. Pat. No. 4,572,594.

SUMMARY OF THE INVENTION

An object of the present invention is to provide a support stand for equipment used in performing videoendoscopic medical procedures including a television monitor.

A further object of the invention is to provide such a support stand that will be mobile, thereby suitable for use on either side of an operating table.

A further object of the invention is to provide such a support stand including cabinetry pivotal to face either left or right while used on either side of an operating table.

A still further object of the present invention is to provide a support stand including television monitor support means movable so that it may be placed in optional optimal positions for viewing by the user.

A still further object of the present invention is to provide such a support stand that will accommodate procedural efficiency, viewing comfort and overall maneuverability.

A still further object of the present invention is to provide such a support stand that will be safe and stable during use, notwithstanding the various positions in which the user may place specific items of equipment.

My videoendoscopic support stand comprises a base defining a support area and a vertical support column mounted on the base within the support area. Horizontal cabinet support means are rigidly secured to the support column. A cabinet having a base, opposite sides, a front, a top and shelves extending between the sides for supporting equipment for use in performing videoendoscopic procedures, is pivotally mounted on the cabinet support means. The cabinet is rotatable between a first cabinet position and a second cabinet position to facilitate access by a user to equipment supported in the cabinet.

The support stand further comprises television monitor support means including a television monitor support arm pivotally mounted atop the support column for supporting a television monitor in position for viewing by a user performing the procedures. The television monitor support arm is rotatable between a first arm position and a second arm position, the first and second arm positions being on the opposite side of the support column from the first and second cabinet positions. The first and second arm positions and the first and second cabinet positions are selected so that the center of gravity of the stand, the television monitor and the equipment supported in the cabinet lies within the support area of the base.

Preferably, the videoendoscopic support stand includes cabinet support means which comprise a pair of vertically-spaced horizontally-extending cabinet support arms. The cabinet is mounted vertically between the arms and is rotatable with respect thereto.

The support stand may further comprise stop means for limiting rotation of the cabinet. The stop means preferably comprise a horizontal plate mounted on at least one of the cabinet support arms. The plate preferably includes at least one pair of peripherally-disposed notches. One of the pair of notches corresponds to the first cabinet position and the other of the pair of notches corresponds to the second cabinet position. The stop means further comprises selective notch-engaging means mounted on the cabinet. The notch-engaging means is selectively operable to engage each of the pair of notches, thereby selectively to retain the cabinet at each of the first and second cabinet positions.

Preferably, the television monitor support arm comprises a first arm pivotally mounted atop the support column and a second arm pivoted at one end thereof on the first arm for movement between an extreme extended position relative to the first arm and a folded position extending back along the first arm. A monitor support tray is preferably pivotally mounted at the other end of the second arm. The tray is adapted to support a television monitor suitable for videoendoscopic medical procedures.

The first arm preferably comprises a longitudinally-extending portion and a socket. The longitudinally-extending portion is attached to the socket. The support column is received within the socket. The second arm is pivoted to the longitudinally-extending portion of the first arm.

The socket preferably comprises a circumferentially-extending notch at its support column-receiving end. One transverse extremity of the circumferentially-extending notch corresponds to the first arm position. The other transverse extremity of the circumferentially-extending notch corresponds to the second arm position. Preferably, the stand comprises stop means for limiting rotation of the first arm. The stop means comprises means to engage the extremities of the circumferentially-extending notch, thereby to restrain the first arm from rotating beyond the first and second arm positions.

The base of the stand preferably comprises three radially-extending legs. Each of the legs contacts a support surface at a surface-contacting point. The legs preferably intersect at a point of intersection centrally located within the support area. The support column is mounted at the point of intersection of the legs. The support area of the base is thus the area of the triangle defined by the surface-contacting points of the legs.

The three radially-extending legs preferably comprise first and second equal-sized legs positioned at right angles to each other, and a third leg, the length of the third leg being less than the length of the first and second legs. The cabinet is mounted on the cabinet support means horizontally between the first and second legs.

Finally, a lockable caster is mounted on each of the radially-extending legs at the surface-contacting point thereof.

BRIEF DESCRIPTION OF THE DRAWINGS

FIG. 5 is a sectional view to an enlarged scale of the support column and television monitor support arm in the position shown in FIG. 2; and FIG. 6 is a sectional view taken on line 6—6 of FIG. 5.

DESCRIPTION OF THE PREFERRED EMBODIMENT

Figure 1:
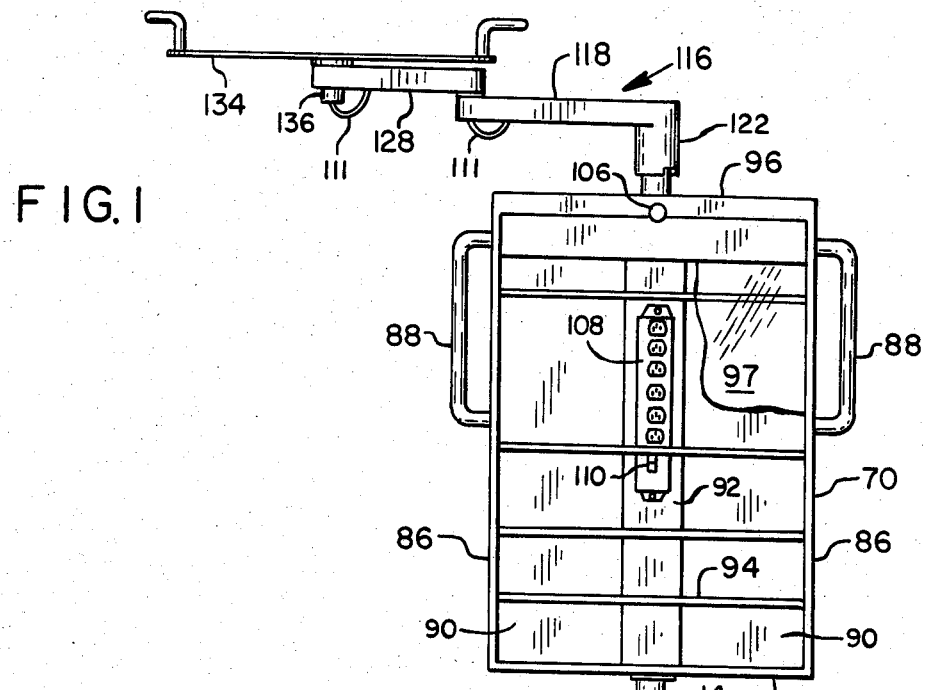
FIG. 1 is a front elevational view of my video-endoscopic support stand.

Referring to the drawings, my videoendoscopic support stand includes a base 10 defining a support area 12 and includes a vertical support column 14. Base 10 preferably comprises three radially-extending legs 16, 18, 20. Legs 16, 18 are positioned at right angles to each other and are longer than leg 20. Each of the legs 16, 18, 20 is triangular in cross section and includes a horizontal member 22, 24, 26 and vertical members 28, 30, 32, respectively. A truncated tubular member 34 is welded to horizontal leg members 22, 24, 26 at their point of intersection. Vertical legs members 28, 30, 32 are welded to tubular member 34 and are tapered toward their extremities, as shown. The extremities of horizontal leg members 22, 24, 26 are rounded and rest on swivel ball-bearing locking casters 36, thereby to make the stand easy to maneuver. The points of contact 38 of casters 36 define a triangular base area 40 for the stand. In a preferred embodiment legs 16, 18 are 25 inches long and leg 20 is 16 inches long. The stand thus occupies a rectangular area 41 of about 36 inches by 40 inches. In this embodiment member 34 is preferably made four inches in diameter at its base and is four inches long.

Support column 14 comprises a tubular member 42 received in a counterbore 44 in member 34 and is fixed thereto by a roll pin 46. In a preferred embodiment member 42 is two inches in diameter and 48 inches long and is provided with a set screw-receiving groove 48 at its upper end 50 for a purpose to be hereinafter described.

Cabinet support means comprising a pair of vertically-spaced horizontal support arms 52, 54 are welded to member 42 as shown. The upper arm 52 includes a first member 56 of square tubular construction welded to member 42 at its end 58. Member 56 is 45° chamfered at 60 for welded attachment to a flat plate 62. Plate 62 is preferably constructed in the form of a pie-shaped sector, the peripheral edge 64 of which includes three notches 66, 67, 68 as shown. Notches 66 and 68 correspond to the extreme rotated positions of cabinet 70; notch 67 corresponds to the central position of cabinet 70, as will be more fully described hereinafter.

The lower cabinet support arm 54 includes a member 72 of square tubular construction welded to member 42 at its end 74 and to a cylindrical tubular member 76 at its distal end 78. Member 76 constitutes a pivot point for cabinet 70.

Cabinet 70 includes a flat base plate 80. A pair of laterally-spaced sheet metal panels 86 define opposite side walls of the cabinet. A pair of U-shaped handle members 88 are mounted one on each side panel 86 near the top of the cabinet. A pair of rear access doors 90 provide easy access to electrical equipment and apparatus appurtenant thereto. A sheet metal panel 92 covers the back of cabinet 70. Doors 90 are hinged on panel 92. Slidable shelves 94 are mounted in the cabinet. Cabinet 70 has a top panel 96 whose outlines in plan form conform to the front, sides and back of the cabinet, as shown. Cabinet 70 is provided with a lockable clear plastic front 97.

Cabinet base plate 80 is provided with a vertical pivot 98 which is received in tubular member 76 of lower support arm 54. Cabinet 70 is also provided with a pivot 100 mounted between a pair of supports 101. Pivot 100 is received in a corresponding aperture 102 in plate 62 received between supports 101. Cabinet 70 is thus pivotally supported by plate 62 and member 76. Cabinet 70 is provided with a spring mounted plunger 104 and a forwardly-extending latch pull 106. Plunger 104 is adapted selectively to engage any one of notches 66, 67, 68, thereby selectively to retain cabinet 70 in a central position (notch 67) or pivoted to face left or right (notches 66 or 68) at the option of the user.

Figure 3:
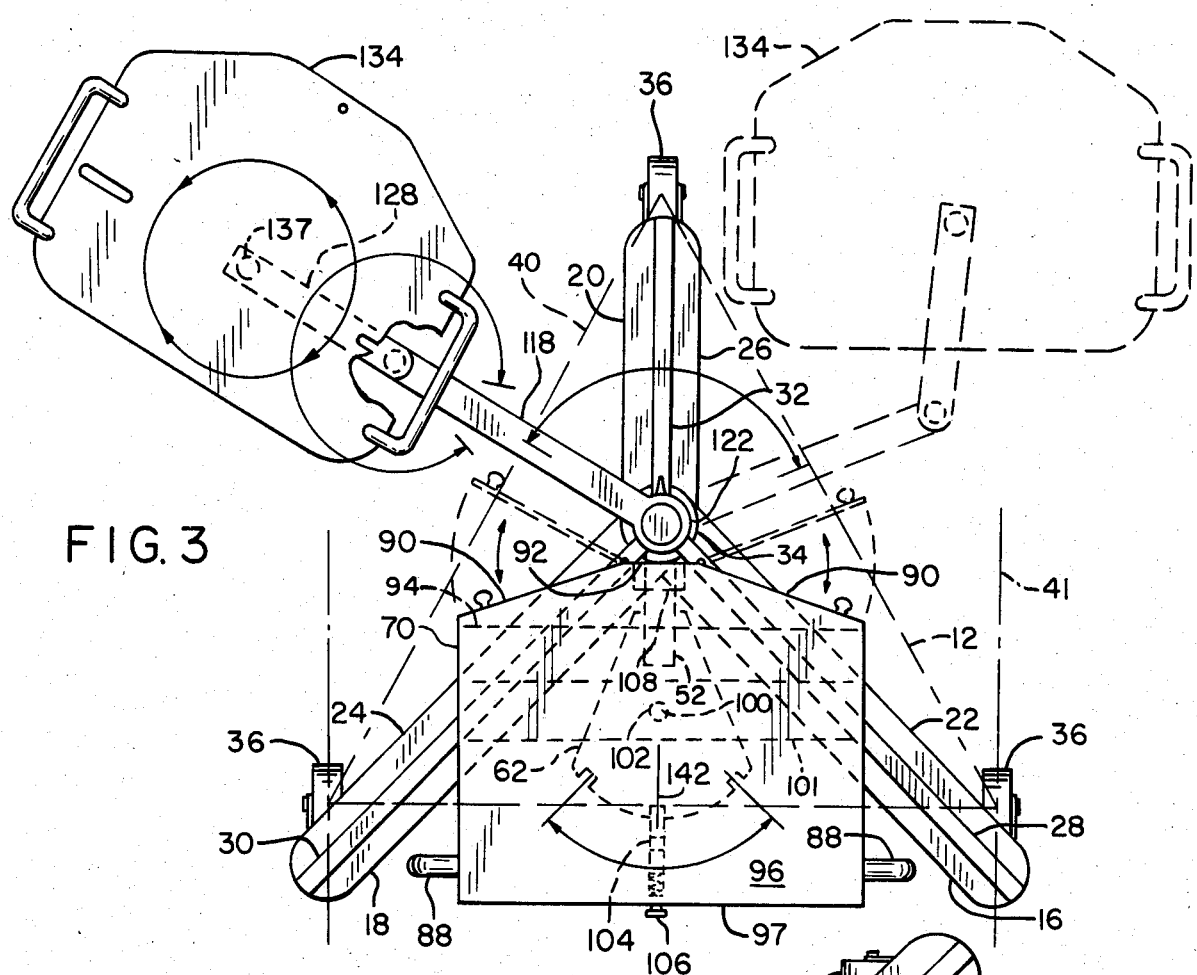
FIG. 3 is a top view of the stand shown with the television monitor support arm shown in the first position in solid lines and in the second position in dashed lines.
Figure 4:
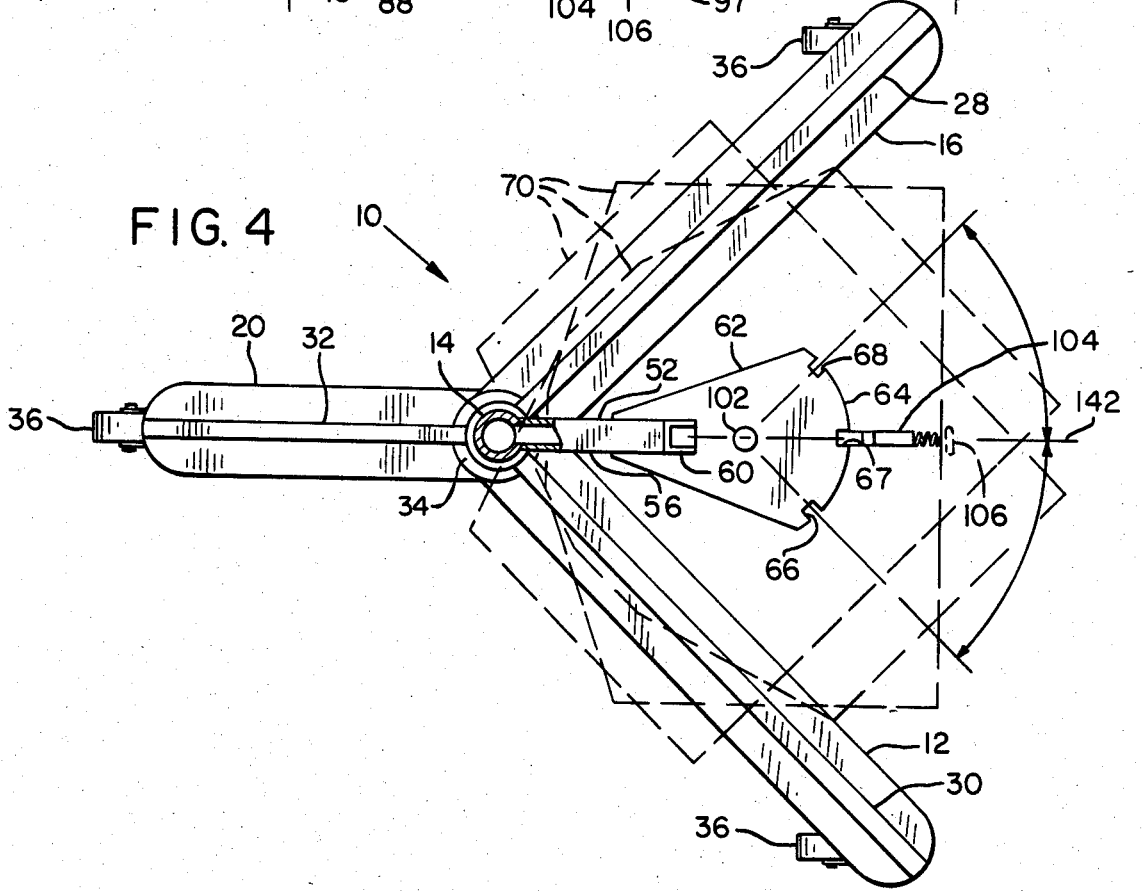
FIG. 4 is a sectional view taken on line 4—4 of FIG. 2.

Shelves 94 extend rearwardly to the extent shown in FIG. 3 to provide room for an electrical strip 108 and a master power switch/circuit breaker 110 at the rear of cabinet 70. The construction allows for adequate electrical equipment ventilation. Electrical line 111 from equipment mounted on shelves 94 can pass interiorly of upper cabinet support member 56 through a hole 112 in vertical support member 42 and thence, upwardly to a television monitor 114 as will hereinafter be described. See FIG. 5.

A television monitor support arm 116 is pivotally mounted atop support member 42 for supporting monitor 114. Arm 116 includes a first arm 118 including a longitudinal portion 120 fabricated of square tubing welded to a tubular socket 122 which receives the upper end 50 of support member 42. The latter is retained by a set screw 124 which engages groove 48. The distal end of portion 120 is welded to another tubular member 126. A second arm 128 includes a depending male member 130 receivable in member 126. The distal end of arm 128 is welded to a tubular member 132.

Figure 2:
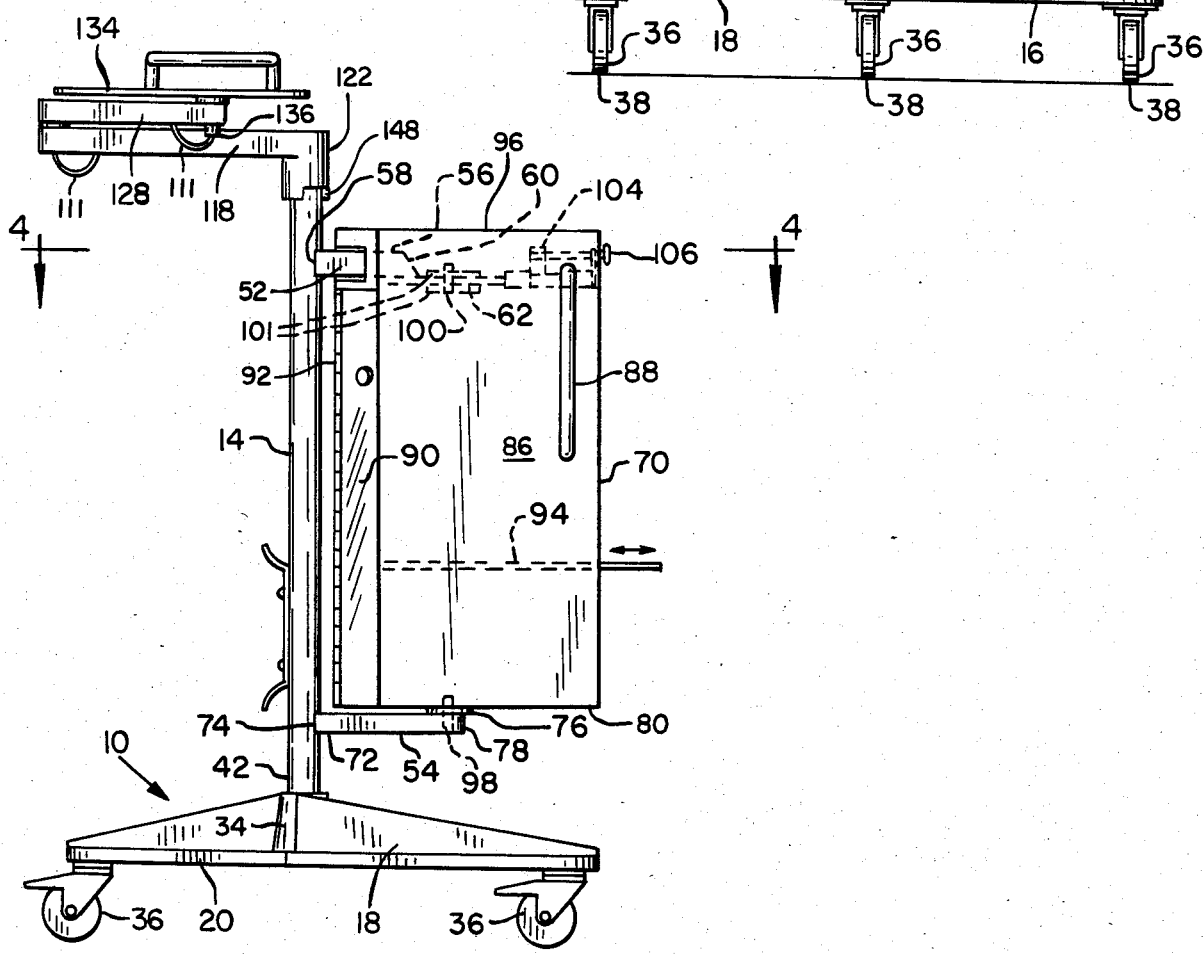
FIG. 2 is a side view of the stand.

A television monitor support tray 134 is supported on a pivot 136 received in an aperture 137. Pivot 136 in turn is received in member 132 and extends therebelow to serve as a stop to prevent 360° rotation of arm 128 with respect to arm 118. Arm 128 thus is able to move between an extreme extended position relative to arm 118 (see solid line position in FIG. 3) and a folded position extending back therealong (see FIGS. 2 and 5).

Socket 122 includes a circumferentially-extending 135° notch 138 at its lower end 140. Notch 138 is symmetrically disposed as respects member 42, on the same side of member 42 as cabinet 70, and extends equal arcuate amounts on opposite sides of center line 142. Thus, one transverse extremity 144 of notch 138 corresponds to one maximum rotated position of arm 118, and the other extremity 146 corresponds to the other maximum rotated position and these positions insure that television monitor support arm 118 remains on the opposite side of vertical support column 14 from the positions occupied by cabinet 70 when pivoted either left or right as hereinabove described. A stop screw 148 (see FIGS. 5 and 6) centered on member 42 adjacent end 140 of socket 122 is engageable with extremities 144, 146 to limit rotation of arm 118 to the 135° arc. In a preferred embodiment arm 118 is sixteen inches long and arm 128 is ten inches long. Notwithstanding arm 128 is positioned in its most forwardly extending position with respect to arm 118, the center of gravity of the entire stand, the monitor 114 and the equipment supported in cabinet 70 will continue to lie within the base area 40, thereby to maintain stability of the assemblage. Furthermore, maximum extension of arm 128 relative to arm 118 while the latter is at one of its maximum rotated positions, coupled with rotation of cabinet 70 to its maximum rotated position in the same direction, will also result in the center of gravity of the entire assembly lying within base area 40. Safety and stability of the assembly is thus assured irrespective of the various positions in which the equipment may be placed.

As mentioned previously, electrical line 111 from equipment positioned on shelves 94 passes interiorly of arm 56, through hole 112 in member 42. The line then passes upwardly through member 42, through socket 122, arm 118 and thence, downwardly through a hole 150 in arm 118, upwardly through tubular member 126, interiorly of member 130, thence interiorly through arm 128, downwardly through a hole 152 therein, and finally upwardly through tubular member 132, pivot 136 and aperture 137 in tray 134, whence connection is made to monitor 114. See FIG. 5. Electrical line 111 is thus conveniently stored to avoid entangling.

My support stand is thus seen to accomplish the objects hereinabove set forth. Having disclosed an operative embodiment, it is to be understood that the apparatus shown is merely illustrative. Changes may be made as desired, as are within the scope of the following claims.

I claim:

1. A videoendoscopic support stand, comprising:
a base defining a support area;
a vertical support column mounted on the base within the support area;
horizontal cabinet support means rigidly secured to the support column;
a cabinet having a base, opposite sides, a front, a top and shelves extending between the sides for supporting equipment for use in performing videoendoscopic medical procedures, the cabinet being pivotally mounted on the cabinet support means, the cabinet being rotatable between a first cabinet position and a second cabinet position to facilitate access by a user to equipment supported in the cabinet; and
television monitor support means including a television monitor support arm pivotally mounted atop the support column for supporting a television monitor in position for viewing by a user performing videoendoscopic medical procedures, the television monitor support arm being rotatable between a first arm position and a second arm position, the first and second arm positions being on the opposite side of the support column from the first and second cabinet positions, the first and second arm positions and the first and second cabinet positions being selected so that the center of gravity of the stand, the television monitor and the equipment supported in the cabinet lies within the support area of the base.

2. A videoendoscopic support stand as in claim 1, in which the cabinet support means comprise a pair of vertically-spaced horizontally-extending cabinet support arms and the cabinet is mounted vertically between the arms, the cabinet being rotatable with respect thereto.

3. A videoendoscopic support stand as in claim 2, further comprising stop means for limiting rotation of the cabinet, the stop means comprising:
a horizontal plate mounted on at least one of the cabinet support arms, the plate including at least one pair of peripherally-disposed notches, one of the pair of notches corresponding to the first cabinet position and the other of the pair of notches corresponding to the second cabinet position; and
selective notch-engaging means mounted on the cabinet, the notch-engaging means being selectively operable to engage each of the pair of notches, thereby selectively to retain the cabinet at each of the first and second cabinet positions.

4. A videoendoscopic support stand as in claim 1 in which the television monitor support arm comprises
a first arm pivotally mounted atop the support column;
a second arm pivoted at one end thereof on the first arm for movement between an extreme extended position relative to the first arm and a folded position extending back along the first arm; and
a television monitor support tray pivotally mounted at the other end of the second arm, the tray being adapted to support a television monitor.

5. A videoendoscopic support stand as in claim 4, further comprising
stop means for limiting rotation of the first arm;
the first arm comprising a longitudinally-extending portion and a socket, the longitudinally-extending portion of the first arm being attached to the socket, the support column being received within the socket, the second arm being pivoted to the longitudinally-extending portion of the first arm;
the socket comprising a circumferentially-extending notch at its support column-receiving end, one transverse extremity of the circumferentially-extending notch corresponding to the first arm position, the other transverse extremity of the circumferentially-extending notch corresponding to the second arm position;
the stop means comprising means to engage the extremities of the circumferentially-extending notch, thereby to restrain the first arm from rotating beyond the first and second arm positions.

6. A videoendoscopic support stand as in claim 1, in which the base comprises three radially-extending legs, each of the legs contacting a support surface at a surface-contacting point, the legs intersecting at a point of intersection centrally located within the support area of the base, the support column being mounted at the point of intersection of the legs, the support area of the base being the area of the triangle defined by the surface-contacting points of the legs.

7. A videoendoscopic support stand as in claim 6, in which the three radially-extending legs comprise
first and second equal-sized legs positioned at right angles to each other, and
a third leg, the length of the third leg being less than the length of the first and second legs, the cabinet being mounted on the cabinet support means horizontally between the first and second legs.

8. A videoendoscopic support stand as in claim 7, further comprising a lockable caster mounted on each of the radially-extending legs at the surface-contacting point thereof.

9. A videoendoscopic support stand, comprising:
- a base defining a support area, the base comprising three radially-extending legs, each of the legs contacting a support surface at a surface-contacting point, the legs comprising first and second equal-sized legs positioned at right angles to each other and a third leg, the length of the third leg being less than the length of the first and second legs, the legs intersecting at a point of intersection centrally located within the support area of the base, the support area of the base being the area of the triangle defined by the surface-contacting points of the legs;
- a lockable caster mounted on each of the radially-extending legs at the surface-contacting point thereof;
- a vertical support column mounted on the base within the support area, the support column being mounted at the point of intersection of the legs;
- horizontal cabinet support means rigidly secured to the support column, the cabinet support means comprising a pair of vertically-spaced horizontally-extending cabinet support arms;
- a cabinet having a base, opposite sides, a front, a top and shelves extending between the sides for supporting equipment for use in performing videoendoscopic medical procedures, the cabinet being pivotally mounted on the cabinet support means vertically between the cabinet support arms and horizontally between the first and second legs of the base, the cabinet being rotatable between a first cabinet position and a second cabinet position to facilitate access by a user to equipment supported in the cabinet;
- first stop means for limiting rotation of the cabinet to the first and second cabinet positions, the first stop means comprising a horizontal plate mounted on at least one of the cabinet support arms, the plate including at least one pair of peripherally-disposed notches, one of the pair of notches corresponding to the first cabinet position and the other of the pair of notches corresponding to the second cabinet position, and selective notch-engaging means mounted on the cabinet, the notch-engaging means being selectively operable to engage each of the pair of notches, thereby selectively to retain the cabinet at each of the first and second cabinet positions;
- television monitor support means including a television monitor support arm pivotally mounted atop the support column for supporting a television monitor in position for viewing by a user performing videoendoscopic medical procedures, the television monitor support arm comprising a first arm pivotally mounted atop the support column, the first arm comprising a longitudinally-extending portion and a socket, the longitudinally-extending portion of the first arm being attached to the socket, the support column being received within the socket, a second arm pivoted at one end thereof on the longitudinally-extending portion of the first arm for movement between an extreme extended position relative to the first arm and a folded position extending back along the first arm, the socket comprising a circumferentially-extending notch at its support column-receiving end, one transverse extremity of the circumferentially-extending notch corresponding to a first arm position of the television monitor support arm, the other transverse extremity of the circumferentially-extending notch corresponding to a second arm position of the television monitor support arm, the first and second arm positions of the television monitor support arm being on the opposite side of the support column from the first and second cabinet positions;
- second stop means for limiting rotation of the first arm of the television monitor support arm, the second stop means comprising means to engage the extremities of the circumferentially-extending notch, thereby to restrain the first arm of the television monitor support arm from rotating beyond the first and second arm positions; and
- a television monitor support tray pivotally mounted at the other end of the second arm of the television monitor support arm, the tray being adapted to support a television monitor;
- the first and second arm positions of the television monitor support arm and the first and second cabinet positions being selected so that the center of gravity of the stand, the television monitor and the equipment supported in the cabinet lies within the support area of the base.

* * * * *